United States Patent [19]

Hoffman et al.

[11] Patent Number: 5,002,537
[45] Date of Patent: Mar. 26, 1991

[54] HYPODERMIC SYRINGE

[75] Inventors: J. Kenneth Hoffman, Warren, Pa.; Joseph W. Blake, III, New Canaan, Conn.

[73] Assignee: GTE Products Corporation, Stamford, Conn.

[21] Appl. No.: 425,149

[22] Filed: Oct. 23, 1989

[51] Int. Cl.$^5$ .............................................. A61M 5/00
[52] U.S. Cl. ...................................... 604/232; 604/234
[58] Field of Search ............................... 604/232–235, 604/229

[56] References Cited

U.S. PATENT DOCUMENTS

| Re. 16,836 | 12/1927 | Cook | 604/232 |
| 2,956,563 | 10/1960 | Sarnoff | 604/232 |
| 3,144,178 | 8/1964 | Sarnoff | 604/235 |
| 4,333,456 | 6/1982 | Webb | 604/232 |
| 4,834,717 | 5/1989 | Haber et al. | 604/195 |
| 4,931,040 | 6/1990 | Haber et al. | 604/110 |

FOREIGN PATENT DOCUMENTS

| 562017 | 5/1960 | Belgium | 604/232 |
| 2950140 | 6/1981 | Fed. Rep. of Germany | 604/235 |
| 923723 | 4/1963 | United Kingdom | 604/234 |

Primary Examiner—C. Fred Rosenbaum
Assistant Examiner—Sharon Rose
Attorney, Agent, or Firm—William H. McNeill

[57] ABSTRACT

An inner elongated tubular member, a plurality of arms which extend through openings in the elongated tubular member and a concentric outer sleeve moveable relative to the inner tubular member for urging each of the arms into engagement with the hub of a needle attached to one end of a cartridge to lock the cartridge and its needle relative to the tubular member and form a hypodermic needle.

22 Claims, 4 Drawing Sheets

HYPODERMIC SYRINGE

BACKGROUND OF THE INVENTION

1. Field of the Invention

The present invention relates to a device for holding a cartridge having a needle attached thereto and for dispensing medicament from the cartridge or drawing blood into the cartridge. When coupled together, the holding device, cartridge and needle form a hypodermic syringe.

2. Description of the Prior Art

One form of hypodermic syringe typically includes a generally cylindrical barrel including a piston rod therein. The rod includes a handle at one end to facilitate reciprocating movement of the rod within the cylindrical barrel. In such a hypodermic syringe a cartridge is provided having a needle attached thereto, the cartridge being inserted into the cylindrical barrel to work in combination with the piston rod to dispense or receive liquid such as medicament or blood, respectively, in response to movement of the piston rod within the barrel. In this form of syringe the piston rod is connected to a plunger in the inserted cartridge, axial movement of the piston rod causing corresponding axial movement of the plunger to dispense the medicament from the cartridge or receive blood within the cartridge depending upon whether such movement is a dispensing movement or aspirating movement. Such hypodermic needles are well known in the art and examples include embodiments described in U.S. Pat. Nos. 2,524,367 to Smith and 4,744,790 to Jankowski et al.

One problem that occurs during use of such a hypodermic syringe is that of accidental exposure of the user of the syringe to whatever contaminants might be present upon or within the needle or cartridge after use thereof. For example, in those instances where the needle and cartridge are to be removed from the barrel and disposed of, heretofore it has been necessary for the user to grasp the needle to remove the needle and cartridge assembly from the barrel. Such grasping can expose the attendant to any contaminant which is on the exterior surface of the needle and cartridge, particularly if the attendant is not wearing a glove. In addition, not infrequently the attendant might be accidentally punctured by the needle while attempting to remove the needle and cartridge and corresponding contamination of the user will obviously result. Somewhat related to these problems is the not unlikely possibility that the attendant might drop the needle and cartridge assembly while removing the assembly from the barrel structure resulting in undesirable contamination of the area exposed to the needle and cartridge. A similar problem is the possibility that the needle and cartridge assembly might prematurely fall out of the barrel-like holder during the disposal operation. In any event, accidental contamination of a medical attendant or anyone else can present a serious health problem especially if the contaminant is an infectious disease such as hepatitis, AIDS and the like.

In order to prevent undesirable contamination, it is highly desirable to provide a hypodermic syringe wherein a medical attendant can remove a cartridge and needle assembly from an associated holder without grasping or otherwise touching the assembly. Similarly, it is also desirable to provide a hypodermic syringe wherein a medical attendant can remove such an assembly without the assembly prematurely falling out of the holder as a result of the attendant carelessly attempting to grasp the assembly and without the attendant inadvertently dropping the assembly.

SUMMARY OF THE INVENTION

This invention achieves these and other results by providing apparatus for use with a cartridge to form a hypodermic syringe. The cartridge includes an elongated body having a first end and a second end and having a needle attached to the first end by means of a hub which is attached to one end of the needle. The apparatus comprises an elongated tubular member having one end which includes at least one opening extending through the peripheral surface of the elongated tubular member and an opposite other end. A respective arm is positioned adjacent each respective opening and is configured to extend through such respective opening into the elongated tubular member in a radial direction relative to a longitudinal axis of the elongated tubular member when the apparatus is in locking engagement. The elongated tubular member is configured such that the cartridge is insertable into the elongated tubular member at the second end of the cartridge until the hub is adjacent the openings and the needle is extending from the elongated tubular member in the direction of the longitudinal axis. Means is positioned around the elongated tubular member and is moveable in the direction of the longitudinal axis for urging each arm in a radial direction towards the longitudinal axis, and into locking engagement with the hub when the cartridge has been inserted into the elongated tubular member. Means is associated with the elongated tubular member for dispensing and aspirating the hypodermic syringe which is formed when the cartridge is inserted into and coupled to the elongated tubular member.

DESCRIPTION OF THE PREFERRED EMBODIMENT

The embodiments of this invention which are illustrated in FIGS. 1 to 8 are particularly suited for achieving the objects of this invention. FIGS. 1 to 8 depict apparatus for use with a cartridge to form a hypodermic syringe 2. The cartridge 4 includes an elongated body 6 which is preferably glass. Body 6 includes a first end 8, a second end 10 and a needle 12 which is attached to first end 8 by means of a hub 14 which is attached to one end of the needle in a known manner.

Figure 1:
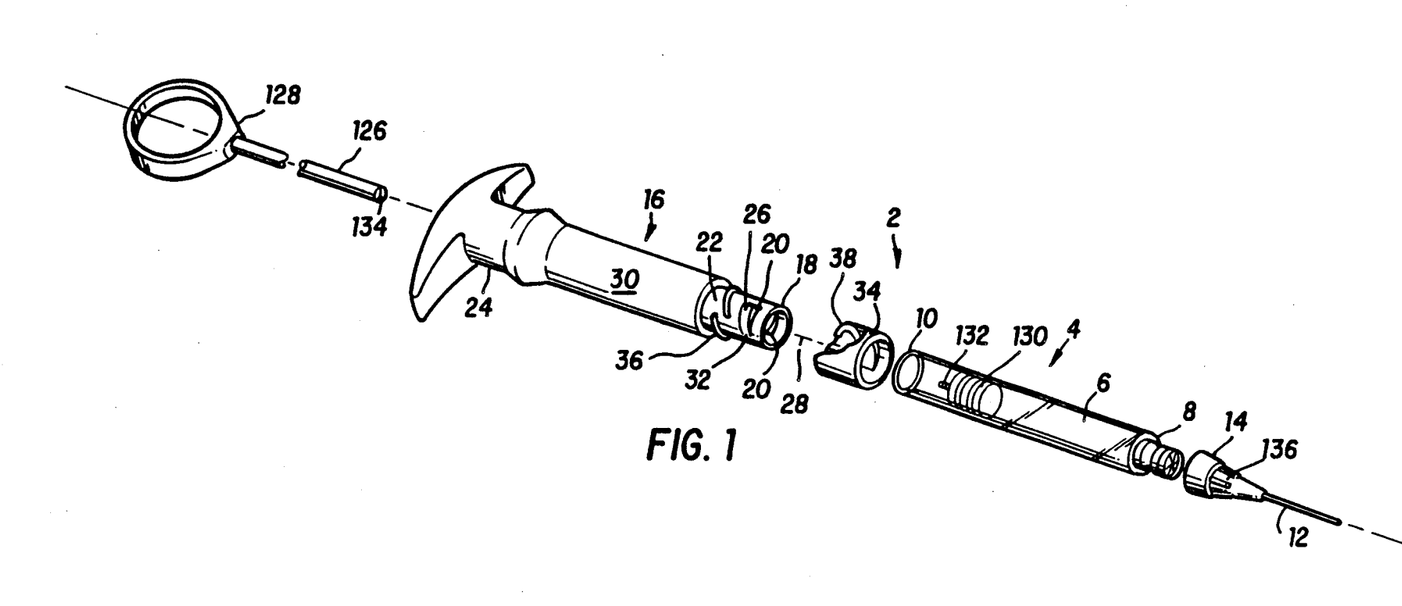
FIG. 1 is an exploded perspective view of one embodiment of the present invention.
Figure 2:
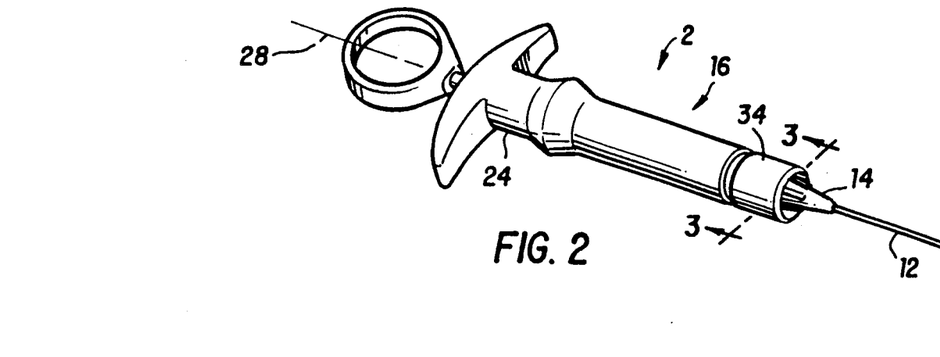
FIG. 2 is an assembled perspective view of the embodiment of FIG. 1 in an open or unlocked position.

In the embodiment of FIGS. 1 and 2, an elongated tubular member 16 is also provided having one end 18 which includes at least one opening 20 extending through the peripheral surface 22 of member 16 and an opposite other end 24. The elongated tubular member 16 is preferably polypropylene.

A respective arm 26 is positioned adjacent each respective opening 20. Each arm 26 is configured to extend through a respective opening 20 into the elongated tubular member 16 at end 18 in a radial direction relative to a longitudinal axis 28 of the member 16 when the apparatus is in locking engagement as explained in detail herein. As will be apparent from the drawings, the elongated tubular member 16 is configured such that the cartridge 4 is insertable into member 16 at the end 10 of the cartridge until the hub 14 is adjacent the openings 20 and the needle 12 extends from member 16 in the direction of axis 28.

The elongated tubular member 16 and each respective arm 26 are formed by a unitary structure. In particular, member 16 is depicted as including a body portion 30 with each respective arm 26 being integrally hinged to body portion 30 at hinge 32 and extending above a respective opening 20 and also away from the body portion 30 at an angle. Preferably, in the embodiment of FIGS. 1 and 2 each arm 26 is resiliently biased away from axis 28 and each opening 20, and each arm 26 generally extends in a circumferential direction relative to longitudinal axis 28.

Figure 3A:
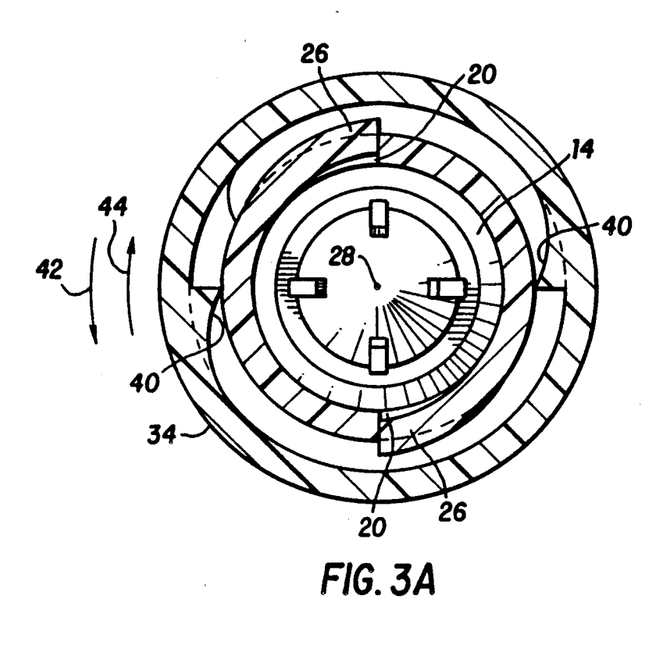
FIGS. 3A and 3B are sectional views taken along 3—3 of FIG. 2 showing the apparatus in a disengaged and an engaged position, respectively.
Figure 3B:
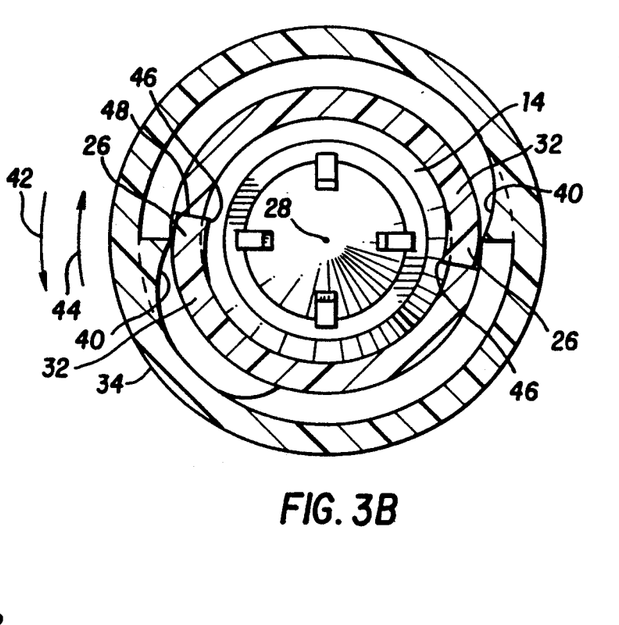

Means moveable in the direction of axis 28 is positioned around the elongated tubular member 16 for urging each arm 26 in a radial direction towards axis 28, and into locking engagement with the hub 14 when the cartridge 4 has been inserted into member 16. For example, the body portion 30 is cylindrical and such urging means comprises a polypropylene sleeve 34. Body portion 30 includes external threads 36 and sleeve 34 includes corresponding internal threads 38. The rotation of sleeve 34 relative to body portion 30 as threads 36 and 38 mesh facilitates movement of sleeve 34 relative to body portion 30 in the direction of axis 28. Such movement can be quickened by providing fast threads 36 and 38. For example, threads 36 and 38 advance the sleeve 34 one half inch for each 360° turn of the sleeve. In addition, the sleeve 34 includes at least one internal cam surface 40 as depicted in FIGS. 3A and 3B. As sleeve 34 is caused to move in one direction of axis 28, each cam surface 40 will engage each respective arm 26 and urge such arm in the radial direction towards longitudinal axis 28, and into locking engagement with hub 14 when the cartridge 4 has been inserted into member 16. For example, FIG. 3A depicts the apparatus of FIGS. 1 and 2 in an unlocked position. The cartridge 4 has been inserted but it will be noted that the arms 26 do not contact hub 14. Rotation of the sleeve 34 in the direction of arrow 42 will cause cam surfaces 40 to engage adjacent arms 26 and by a camming action urge arms 26 in a radial direction towards axis 28 and into locking engagement with hub 14 as depicted in FIG. 3B. To remove cartridge 4 from the apparatus, sleeve 34 is rotated in the direction of arrow 44 to cause cam surfaces 40 to disengage adjacent arms 26. Due to the resiliency of arms 26 they will resume their original position as depicted in FIG. 3A; that is, arms 26 will move in a radial direction away from axis 28 and out of locking engagement with hub 14 so that the cartridge can be readily removed from the apparatus.

In the embodiment of FIGS. 1 and 2, preferably there is a plurality of openings 20, which are equally spaced circumferentially about the peripheral surface 22, and an equal number of corresponding arms 26. Preferably, each arm includes a claw-like member 46 at an end 48 opposite hinge 32. As depicted in FIGS. 3A and 3B it is preferred that the opening 20 include at least one pair of opposing openings.

Figures 4, 5:
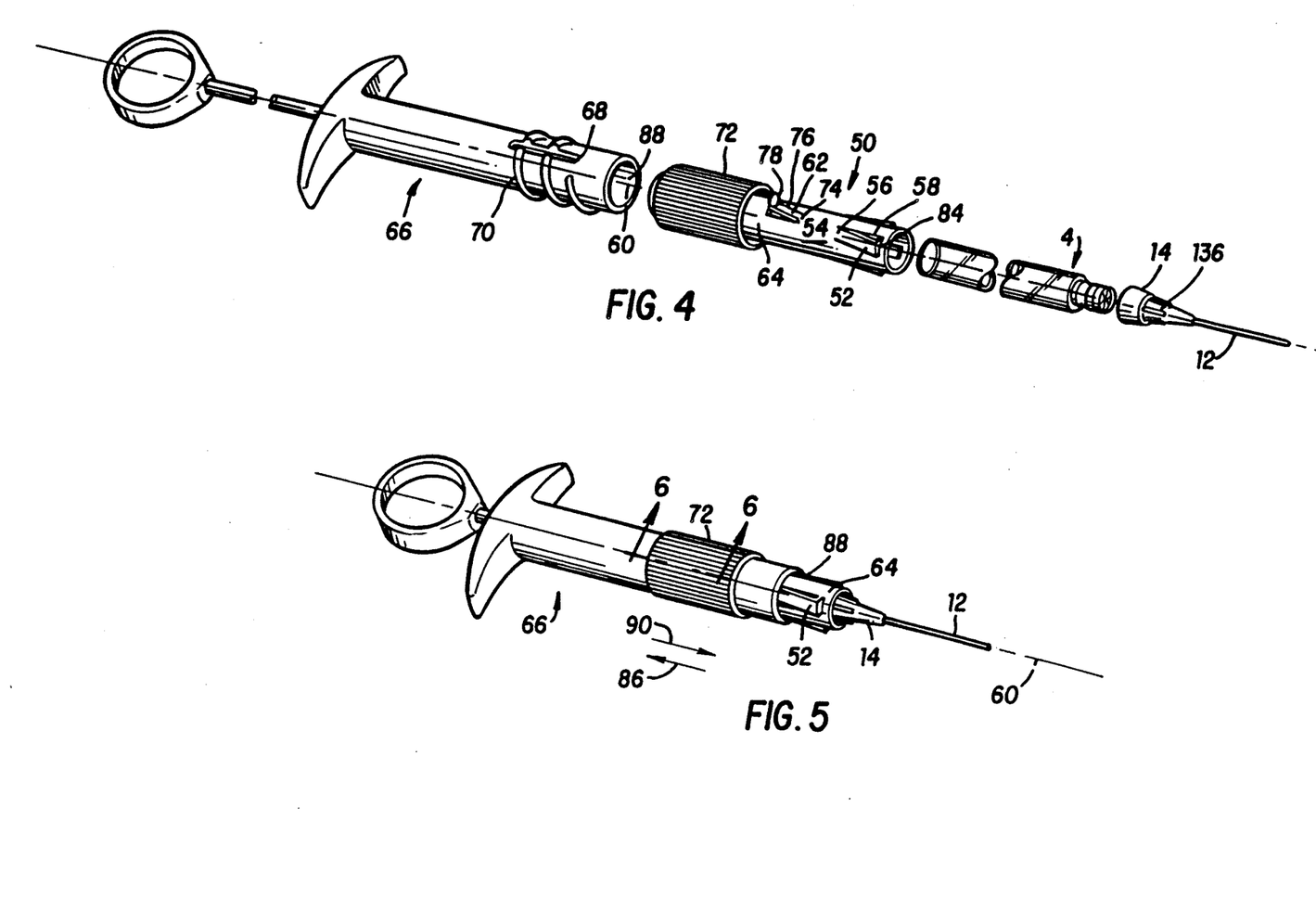
FIG. 4 is an exploded perspective view of another embodiment of the present view.
FIG. 5 is an assembled perspective view of the embodiment of FIG. 4 in a closed or locked position.
Figure 6:
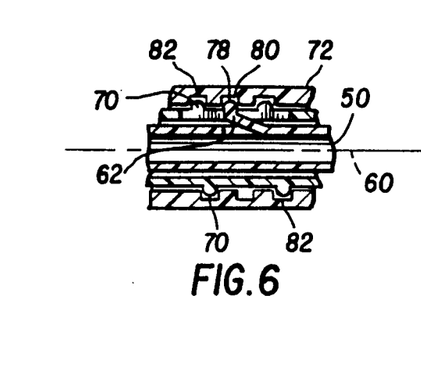
FIG. 6 is a sectional view taken along 6—6 of FIG. 5.

An alternative embodiment is depicted in FIGS. 4 and 5. In this embodiment an elongated tubular member 50 and each respective arm 52 are formed by a unitary structure. In particular, member 50 includes a body portion 54 and a plurality of arms 52. Each arm is integrally hinged at 56 to the body portion and extend from a respective hinge 56 above a respective opening 58 at an angle away from the body portion. As in the embodiment of FIGS. 1 and 2, each arm 52 is resiliently biased away from a longitudinal axis 60 of the elongated tubular member 50. In the embodiment of FIGS. 4 and 5, the openings 58 and corresponding arms 52 extend in the direction of the longitudinal axis 60. Body portion 54 is cylindrical and includes a locking tab 62 extending from an outer surface 64 of the body portion. As in the embodiment of FIGS. 1 and 2, means which is moveable in the direction of axis 60 is positioned around the elongated tubular member 50 for urging each arm 52 in a radial direction towards axis 60, and into locking engagement with the hub 14 of a cartridge 4 when cartridge 4 has been inserted into the elongated tubular member. Such urging means includes an elongated first sleeve 66 into which the elongated tubular member 50 extends. Sleeve 66 includes an elongated keyway 68 which extends in the direction of axis 60 and mates with the locking tab 62 to facilitate movement of the member 50 relative to the sleeve 66 along axis 60. Sleeve 66 also includes external threads 70 which are coextensive with the keyway 68 as depicted in FIG. 4. The urging means also includes a second sleeve 72 into which the first sleeve 66 extends. The second sleeve 72 includes means internal of sleeve 72 which mates with locking tab 62 for moving the elongated tubular member 50 in the direction of axis 60 when sleeve 72 is moved in the direction of axis 60. For example, in the embodiment of FIGS. 4 and 5 the elongated tubular member 50 and the locking tab 62 are formed by a unitary structure. In particular, the locking tab 62 includes one end 74 integrally hinged at the body portion 54 and an opposite second end 76. The locking tab 62 extends at an angle away from body portion 54 from end 74 to end 76. The moving means includes a protuberance 78 at the second end 76 of the locking tab 62 which mates with a corresponding recess 80 in the sleeve 72 as depicted in FIG. 6. The sleeve 72 also includes internal threads 82 which mate with the external threads 70. As depicted in FIGS. 4 and 5 there are a plurality of openings 58 which are equally spaced circumferentially about the peripheral surface 64 to form at least one pair of opposing openings and each arm 52 includes a claw-like member 84 at an end opposite hinge 56. In the preferred embodiment, elongated tubular member 50 and sleeves 66 and 72 are formed from polypropylene.

In the operation of the apparatus of FIGS. 4 and 5 a cartridge 4 is inserted into the elongated tubular member 50 until the hub 14 is adjacent the openings 58. Then the sleeve 72 is axially moved in the direction of arrow 86 by rotating sleeve 72 about axis 60. Such rotation and axial movement is facilitated by corresponding threads 70 and 82. As sleeve 72 is moved in the direction of arrow 86 sleeve 72 causes the elongated tubular member 50 to also move axially in the direction of arrow 86. In essence, sleeve 72 pulls member 50 in the direction of arrow 86 due to the coupling provided by the protuberance 78 which extends into the recess 80. In this manner, the elongated tubular member 50 is drawn into the sleeve 66 such that the inner surface 88 of sleeve 66 engages the arms 52 thereby camming arms 52 in a radial direction towards axis 60 such that the claw-like members 84 are urged into locking engagement with the hub 14 of the cartridge 4. To remove the cartridge from the elongated tubular member 50, sleeve 72 is rotated in the reverse direction causing the sleeve 72 to move in the direction of arrow 90 to thereby remove or push member 50 from sleeve 66 due to the coupling between protuberance 78 and recess 80. As member 50 exits sleeve 66 the resilient arms 52 are no longer cammed by surface 88 and therefore expand away from axis 60 causing the claw-like members 84 to spring out of engagement with the hub 14 so that the cartridge 4 can be readily removed from the apparatus. Threads 70 and 82 are fast threads which advance the sleeve 72 one half inch for each 360° turn of the sleeve.

Figure 7:
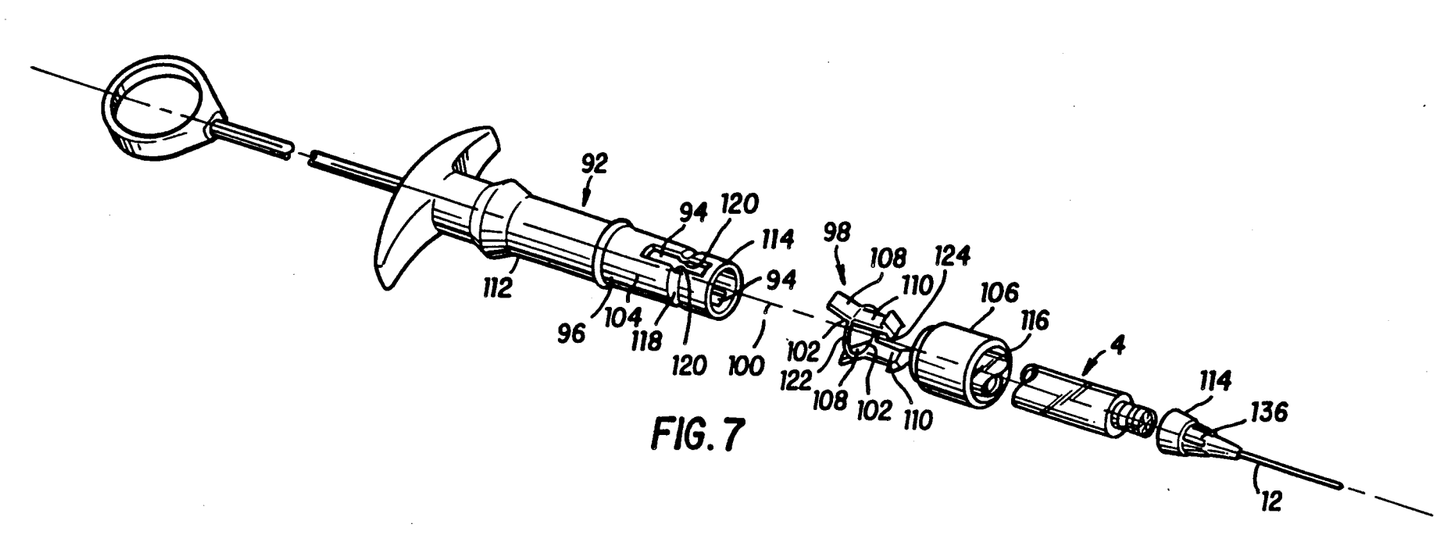
FIG. 7 is an exploded perspective view of yet another embodiment of the present invention.
Figure 8:
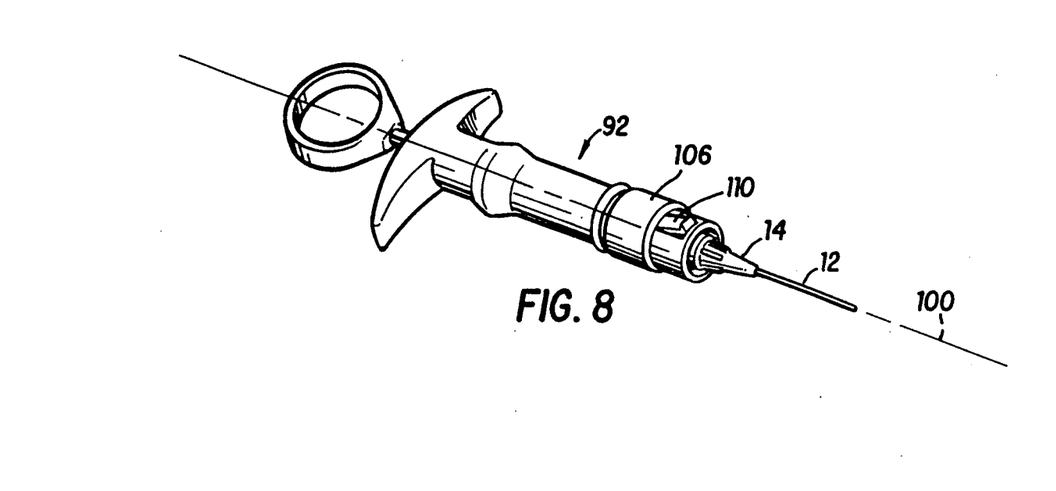
FIG. 8 is an assembled perspective view of the embodiment of FIG. 7 in a closed or locked position.

Another alternative embodiment is depicted in FIGS. 7 and 8. In this embodiment, an elongated tubular member 92 is provided having one end which includes at least one opening 94 extending through the peripheral surface 96. A respective arm 98 is positioned adjacent each respective opening 94. Each arm 98 is configured to extend through a respective opening 94 into the member 92 in a radial direction relative to a longitudinal axis 100 of member 92 when the apparatus is in locking engagement as described herein. In the preferred embodiment each respective arm 98 is generally V-shaped with the closed end 102 of the V extending in the direction of axis 100. Each arm 98 is preferably coextensive with a corresponding opening 94.

Means moveable in the direction of axis 100 is positioned around elongated tubular member 92 for urging each arm in a radial direction towards axis 100 and into locking engagement with the hub 14 of cartridge 4 when the cartridge has been inserted into member 92. For example, the elongated tubular member 92 includes a cylindrical body portion 104, and the urging means includes a sleeve 106 which is slideable relative to the cylindrical body portion. Sleeve 106 will be in engagement with a first extension 108 of the V-shaped arm 98 to pivot a second extension 110 out of the elongated tubular member 92 when the sleeve is moved towards end 112 of member 92. In a like manner, sleeve 106 will be in engagement with the second extension 110 to pivot the second extension 110 into the elongated tubular member 92 when the sleeve is moved towards opposite end 114. In this manner, a reciprocating camming action of an inner surface 116 of sleeve 106 upon extensions 108 and 110 of the V-shaped arm 98 will cause the V-shaped arm to pivot about its closed end 102 respectively out of and into engagement with hub 14 of cartridge 4.

Preferably, the cylindrical body portion 104 includes a groove 118 which extends circumferentially about the peripheral surface 96 and intersects each opening 94 at, for example, 120 as depicted in FIG. 7. In addition, each arm 98 is attached to a ring 122 at a respective closed end 102. Ring 122 forms a snap fit relative to groove 118 and is thereby maintained in groove 118 to hold each respective arm 98 in place relative to a corresponding opening 94.

In the preferred embodiment a plurality of openings 94 are provided which are equally spaced circumferentially of peripheral surface 96. As in the case of the other embodiments herein, each arm 98 can include a claw-like member 124 facing axis 100. Each claw-like member 124 extends from a second extension 110. Preferably, the plurality of openings 94 include at least one pair of opposing openings as depicted in FIG. 7. In the preferred embodiment, elongated tubular member 92, arms 98, ring 122 and sleeve 106 are formed from polypropylene.

In operation, sleeve 106 is moved in the direction of axis 100 towards end 112 causing the surface 116 to effect a camming action vis-a-vis the extensions 108 urging extensions 108 through openings 94 and into member 92 thereby causing extensions 110 to pivot out of member 92. A cartridge 4 is then inserted into the elongated tubular member until the hub 14 is adjacent openings 94 and corresponding arms 98. Then sleeve 106 is moved in the direction of axis 100 towards end 114 whereby the surface 116 effects a camming action vis-a-vis the extensions 110 urging extensions 110 through openings 94 and into the member 92. In essence, the extensions pivot about closed end 102 which is affixed to ring 122. As extensions 110 are urged into member 92, the claw-like members 124 are urged into locking engagement with the hub 14 of the cartridge 4 to hold it in place. To remove the cartridge 4, the sleeve 106 is again moved towards end 112 causing the extensions 108 to pivot into member 92 and the extensions 110 to pivot out of member 92 allowing the claw-like members 124 to disengage the cartridge 4.

All of the embodiments of FIGS. 1 through 8 include means associated with the elongated tubular member for dispensing and aspirating the hypodermic syringe 2 which is formed when cartridge 4 is inserted into and coupled to the elongated tubular member. For example, and by way of example only, the embodiment of FIG. 1 is depicted as including a piston rod 126 having a handle 128 at one end to facilitate reciprocating movement of the rod in a known manner. Similarly, cartridge 4 includes a typical plunger 130 therein which is coupled to the piston rod 126 in a known manner such that axial movement of the piston rod causes corresponding axial movement of the plunger to dispense the medicament from the cartridge or receive blood within the cartridge depending upon whether such movement is a dispensing movement or aspirating movement. Piston rod 126 and handle 128 are preferably formed from acetal. In the embodiment of FIG. 1 the piston rod 126 can be coupled to plunger 130 by means of the threaded protuberance 132 and corresponding threaded bore 134.

In the embodiments depicted in the drawings each cartridge 4 includes a hub 14 which includes at least one, and preferably a plurality, of recessed areas 136, and the plurality of arms include corresponding arms which mate with such areas when the cartridge has been inserted into the elongated tubular member and the arms have been urged into locking engagement with the hub as discussed herein. For example, in the embodiment of FIGS. 1 to 3, claw-like ends 46 mate with recessed areas 136 of hub 14. Hub 14 can be formed from any suitable material but is preferably metal such as stainless steel.

The preferred materials for forming the embodiments of the present invention have been discussed herein. However, the apparatus of the present invention can be formed from any material useful in the manufacture of hypodermic syringes. If desired various components can be transparent so that the content of the cartridge 4 can be viewed. For example, in FIGS. 7 and 8 the elongated tubular member 92 can be transparent.

It will be readily apparent that the present invention provides a hypodermic syringe wherein a medical attendant can remove a cartridge assembly including a needle attached thereto from a holder without grasping or otherwise touching such assembly and without such assembly falling out of the holder as a result of the attendant carelessly attempting to grasp the assembly and without the attendant inadvertently dropping the assembly.

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

We claim:

1. Apparatus for use with a cartridge to form a hypodermic syringe, said cartridge including an elongated body having a first end and a second end and having a needle attached to said first end by means of a hub which is attached to one end of said needle, comprising:

an elongated tubular member having one end which includes at least one opening extending through the peripheral surface of said elongated tubular member and an opposite other end;

a respective arm positioned adjacent each respective opening of said at least one opening and configured to extend through said respective opening into said elongated tubular member in a radial direction relative to a longitudinal axis of said elongated tubular member when said apparatus is in locking engagement, said elongated tubular member being configured such that said cartridge is insertable into said elongated tubular member at said second end of said cartridge until said hub is adjacent said at least one opening and said needle is extending from said elongated tubular member in the direction of said longitudinal axis;

means positioned around said elongated tubular member and being moveable in the direction of said longitudinal axis for urging each arm in said radial direction towards said longitudinal axis and into locking engagement with said hub when said cartridge has been inserted into said elongated tubular member;

means associated with said elongated tubular member for dispensing and aspirating said hypodermic syringe which is formed when said cartridge is inserted into and coupled to said elongated tubular member;

said elongated tubular member and each respective arm being formed by a unitary structure, said elongated tubular member including a body portion, and each respective arm having an integral hinge at said body portion and extending above a respective opening and at an angle away from said body portion at a respective hinge, each respective arm being resiliently biased away from said longitudinal axis, said at least one opening and each respective arm extending in a circumferential direction relative to said longitudinal axis, said body portion being cylindrical and further wherein said urging means comprises a sleeve; and said body portion including external threads, and said sleeve including corresponding internal threads, to facilitate movement of said sleeve relative to said body portion in the direction of said longitudinal axis, and further wherein said sleeve includes at least one internal cam surface each of which engages a respective arm for urging each respective arm in said radial direction towards said longitudinal axis, and into locking engagement with said hub when said cartridge has been inserted into said elongated tubular member, during said longitudinal movement of said sleeve.

2. The apparatus of claim 1 wherein said at least one opening includes a plurality of openings equally spaced circumferentially about said peripheral surface.

3. The apparatus of claim 2 wherein each respective arm includes a claw-like member facing said longitudinal axis at an end of said respective arm opposite said hinge.

4. The apparatus of claim 3 wherein said plurality of openings includes at least one pair of opposing openings.

5. The apparatus of claim 1 wherein said at least one opening includes a plurality of openings equally spaced circumferentially of said peripheral surface.

6. The apparatus of claim 5 wherein each respective V-shaped arm includes a claw-like member facing said longitudinal axis and extending from said second extension of each respective V-shaped arm.

7. The apparatus of claim 6 wherein said plurality of openings includes at least one pair of opposing openings.

8. A hypodermic syringe, comprising:

a cartridge including an elongated body having a first end and a second end and having a needle attached to said first end by means of a hub which is attached to one end of said needle;

an elongated tubular member having one end which includes at least one opening extending through the peripheral surface of said elongated tubular member and an opposite other end;

a respective arm positioned adjacent each respective opening of said at least one opening and configured to extend through said respective opening into said elongated tubular member and in a radial direction relative to a longitudinal axis of said elongated tubular member when said apparatus is in a locking engagement, said elongated tubular member being configured such that said cartridge is inserted into said elongated tubular member at said second end of said cartridge, said hub is adjacent said at least one opening and said needle extends from said elongated tubular member in the direction of said longitudinal axis;

means positioned around said elongated tubular member and being moveable in the direction of said longitudinal axis, for urging each arm in said radial direction towards said longitudinal axis, and into locking engagement with said hub;

means associated with said elongated tubular member for dispensing and aspirating said hypodermic syringe which is formed by said cartridge and said elongated tubular member;

said elongated tubular member and each respective arm being formed by a unitary structure, said elongated tubular member including a body portion, and each respective arm having an integral hinge at said body portion and extending above a respective opening and at an angle away from said body portion at a respective hinge;

each respective arm being resiliently biased away from said longitudinal axis, said at least one opening and each respective arm extending in a circumferential direction relative to said longitudinal axis, said body portion being cylindrical and further wherein said urging means comprises a sleeve.

9. The apparatus of claim 8 wherein said body portion includes external threads, and wherein said sleeve includes corresponding internal threads, to facilitate movement of said sleeve relative to said body portion in the direction of said longitudinal axis, and further wherein said sleeve includes at least one internal cam surface each of which engages a respective arm for urging each respective arm in said radial direction towards said longitudinal axis, and into locking engagement with said hub.

10. Apparatus for use with a cartridge to form a hypodermic syringe, said cartridge including an elongated body having a first end and a second end and having a needle attached to said first end by means of a hub which is attached to one end of said needle, comprising:

an elongated tubular member having one end which includes at least one opening extending through the peripheral surface of said elongated tubular member and an opposite other end;

a respective arm positioned adjacent each respective opening of said at least one opening and configured to extend through said respective opening into said elongated tubular member in a radial direction relative to a longitudinal axis of said elongated tubular member when said apparatus is in locking engagement, said elongated tubular member being configured such that said cartridge is insertable into said elongated tubular member at said second end of said cartridge until said hub is adjacent said at least one opening and said needle is extending from said elongated tubular member in the direction of said longitudinal axis;

means positioned around said elongated tubular member and being moveable in the direction of said longitudinal axis for urging each arm in said radial direction towards said longitudinal axis and into locking engagement with said hub when said cartridge has been inserted into said elongated tubular member;

means associated with said elongated tubular member for dispensing and aspirating said hypodermic syringe which is formed when said cartridge is inserted into and coupled to said elongated tubular member, said elongated tubular member and each respective arm being formed by a unitary structure, said elongated tubular member including a body portion, and each respective arm having an integral hinge at said body portion and extending above a respective opening and at an angle away from said body portion at a respective hinge, each respective arm being resiliently biased away from said longitudinal axis, said at least one opening and each respective arm extending in the direction of said longitudinal axis, and said body portion being cylindrical and including a locking tab extending from an outer surface of said body portion and wherein said urging means includes (1) an elongated first sleeve into which said elongated tubular member extends, said elongated first sleeve having an elongated keyway which extends in the direction of said longitudinal axis and mates with said locking tab to facilitate movement of said elongated tubular member relative to said sleeve along said longitudinal axis, and external threads coextensive with said elongated keyway, and (2) a second sleeve into which said first sleeve extends, said second sleeve having means internal of said second sleeve which mates with said locking tab for moving said elongated tubular member in the direction of said longitudinal axis when said second sleeve is moved in the direction of said longitudinal axis, and internal threads which mate with said external threads to facilitate movement of said second sleeve in the direction of said longitudinal axis when said second sleeve is rotated about said longitudinal axis relative to said external threads.

11. The apparatus of claim 10 wherein said elongated tubular member and said locking tab are formed by a unitary structure, and wherein said locking tab includes one end integrally hinged at said body portion and an opposite second end, said locking tab extending at an angle away from said body portion from said one end to said second end.

12. The apparatus of claim 11 wherein said moving means includes a protuberance at said opposite second end of said locking tab and a mating recess in said second sleeve.

13. The apparatus of claim 12 wherein said at least one opening includes a plurality of openings equally spaced circumferentially about said peripheral surface.

14. The apparatus of claim 13 wherein each respective arm includes a claw-like member facing said longitudinal axis at an end of said respective arm opposite said hinge.

15. The apparatus of claim 14 wherein said plurality of openings includes at least one pair of opposing openings.

16. Apparatus for use with a cartridge to form a hypodermic syringe, said cartridge including an elongated body having a first end and a second end and having a needle attached to said first end by means of a hub which is attached to one end of said needle, comprising:

an elongated tubular member having one end which includes at least one opening extending through the peripheral surface of said elongated tubular member and an opposite other end;

a respective arm positioned adjacent each respective opening of said at least one opening and configured to extend through said respective opening into said elongated tubular member in a radial direction relative to a longitudinal axis of said elongated tubular member when said apparatus is in locking engagement, said elongated tubular member being configured such that said cartridge is insertable into said elongated tubular member at said second end of said cartridge until said hub is adjacent said at least one opening and said needle is extending from said elongated tubular member in the direction of said longitudinal axis;

means positioned around said elongated tubular member and being moveable in the direction of said longitudinal axis for urging each arm in said radial direction towards said longitudinal axis and into locking engagement with said hub when said cartridge has been inserted into said elongated tubular member;

means associated with said elongated tubular member for dispensing and aspirating said hypodermic syringe which is formed when said cartridge is inserted into and coupled to said elongated tubular member;

each respective arm being generally V-shaped with the closed end of said V extending in the direction of said longitudinal axis, and wherein each V-shaped arm is coextensive with a corresponding opening of said at least one opening; and said at least one end of said elongated tubular member including a cylindrical body portion and further wherein said urging means comprises a sleeve, said sleeve being slideable relative to said cylindrical body portion and being in engagement with a first extension of said V-shaped arm to pivot a second extension of said V-shaped arm out of said elongated tubular member when said sleeve is moved towards said opposite other end of said elongated tubular member, and being in engagement with said second extension of said V-shaped arm to pivot said second extension into said elongated tubular member when said sleeve is moved towards said one end of said elongated tubular member thereby camming said V-shaped arm out of and into locking engagement, respectively, with said hub when said cartridge has been inserted into said elongated tubular member.

17. The apparatus of claim 16 wherein said cylindrical body portion includes a groove which extends circumferentially about the peripheral surface of said cylindrical body portion and intersects said at least one opening, and further wherein each respective arm is attached to a ring at each respective closed end, said ring forming a snap fit relative to said groove to hold each respective arm in place relative to each respective opening of said at least one opening.

18. A hypodermic syringe, comprising:

a cartridge including an elongated body having a first end and a second end and having a needle attached to said first end by means of a hub which is attached to one end of said needle;

an elongated tubular member having one end which includes at least one opening extending through the peripheral surface of said elongated tubular member and an opposite other end;

a respective arm positioned adjacent each respective opening of said at least one opening and configured to extend through said respective opening into said elongated tubular member and in a radial direction relative to a longitudinal axis of said elongated tubular member when said apparatus is in a locking engagement, said elongated tubular member being configured such that said cartridge is inserted into said elongated tubular member at said second end of said cartridge, said hub is adjacent said at least one opening and said needle extends from said elongated tubular member in the direction of said longitudinal axis;

means positioned around said elongated tubular member and being moveable in the direction of said longitudinal axis, for urging each arm in said radial direction towards said longitudinal axis, and into locking engagement with said hub, and;

means associated with said elongated tubular member for dispensing and aspirating said hypodermic syringe which is formed by said cartridge and said elongated tubular member, said elongated tubular member and each respective arm being formed by a unitary structure, said elongated tubular member including a body portion, and each respective arm having an integral hinge at said body portion and extending above a respective opening at an angle away from said body portion at a respective hinge, said at least one opening and each respective arm extending in the direction of said longitudinal axis, said body portion being cylindrical and including a locking tab extending from an outer surface of said body portion and wherein said urging means includes (1) an elongated first sleeve into which said elongated tubular member extends, said elongated first sleeve having an elongated keyway which extends in the direction of said longitudinal axis and mates with said locking tab to facilitate movement of said elongated tubular member relative to said sleeve along said longitudinal axis, and external threads coextensive with said elongated keyway, and (2) a second sleeve into which said first sleeve extends, said second sleeve having means internal of said second sleeve which mates with said locking tab for moving said elongated tubular member in the direction of said longitudinal axis when said second sleeve is moved in the direction of said longitudinal axis, and internal threads which mate with said external threads to facilitate movement of said second sleeve in the direction of said longitudinal axis when said second sleeve is rotated about said longitudinal axis relative to said external threads.

19. The apparatus of claim 18 wherein said elongated tubular member and said locking tab are formed by a unitary structure, and wherein said locking tab includes one end integrally hinged at said body portion and an opposite second end, said locking tab extending at an angle away from said body portion from said one end to said second end.

20. The apparatus of claim 19 wherein said moving means includes a protuberance at said opposite second end of said locking tab and a mating recess in said second sleeve.

21. A hypodermic syringe, comprising:

a cartridge including an elongated body having a first end and a second end and having a needle attached to said first end by means of a hub which is attached to one end of said needle;

an elongated tubular member having one end which includes at least one opening extending through the peripheral surface of said elongated tubular member and an opposite other end;

a respective arm positioned adjacent each respective opening of said at least one opening and configured to extend through said respective opening into said elongated tubular member and in a radial direction relative to a longitudinal axis of said elongated tubular member when said apparatus is in a locking engagement, said elongated tubular member being configured such that said cartridge is inserted into said elongated tubular member at said second end of said cartridge, said hub is adjacent said at least one opening and said needle extends from said elongated tubular member in the direction of said longitudinal axis;

means positioned around said elongated tubular member and being moveable in the direction of said longitudinal axis, for urging each arm in said radial direction towards said longitudinal axis, and into locking engagement with said hub;

means associated with said elongated tubular member for dispensing and aspirating said hypodermic syringe which is formed by said cartridge and said elongated tubular member, each respective arm being generally V-shaped with the closed end of said V extending in the direction of said longitudinal axis, and wherein each V-shaped arm is coextensive with a corresponding opening of said at least one opening, said at least one end of said elongated tubular member including a cylindrical body portion and further wherein said urging means comprises a sleeve, said sleeve being slideable relative to said cylindrical body portion and being in engagement with a first extension of said V-shaped arm to pivot a second extension of said V-shaped arm out of said elongated tubular member when said sleeve is moved towards said opposite other end of said elongated tubular member, and being in engagement with said second extension of said V-shaped arm to pivot said second extension into said elongated tubular member when said sleeve is moved towards said one end of said elongated tubular member thereby camming said V-shaped arm out of and into locking engagement, respectively, with said hub.

22. The apparatus of claim 21 wherein said cylindrical body portion includes a groove which extends circumferentially about the peripheral surface of said cylindrical body portion and intersects said at least one opening, and further wherein each respective arm is attached to a ring at each respective closed end, said ring forming a snap fit relative to said groove to hold each respective arm in place relative to each respective opening of said at least one opening.

* * * * *